United States Patent
Ryan

(10) Patent No.: US 9,050,049 B2
(45) Date of Patent: Jun. 9, 2015

(54) URETHRA GAUGE AND METHODS OF MANUFACTURE, AND OPERATION THEREOF

(76) Inventor: Daniel David Ryan, Chadds Ford, PA (US)

(*) Notice: Subject to any disclaimer, the term of this patent is extended or adjusted under 35 U.S.C. 154(b) by 730 days.

(21) Appl. No.: 12/483,008

(22) Filed: Jun. 11, 2009

(65) Prior Publication Data
US 2010/0016760 A1    Jan. 21, 2010

Related U.S. Application Data

(60) Provisional application No. 61/061,086, filed on Jun. 12, 2008.

(51) Int. Cl.
- A61B 5/103 (2006.01)
- A61B 5/00 (2006.01)
- A61B 5/107 (2006.01)

(52) U.S. Cl.
CPC ............... *A61B 5/411* (2013.01); *Y10T 29/49* (2015.01); *A61B 5/1076* (2013.01)

(58) Field of Classification Search
CPC ..................................................... A61B 5/1076
USPC ................ 600/587, 591, 593; 33/511, 512
See application file for complete search history.

(56) References Cited

U.S. PATENT DOCUMENTS

| | | | |
|---|---|---|---|
| 1,264,519 A * | 4/1918 | Hinson | 72/477 |
| 3,740,779 A * | 6/1973 | Rubricuis | 7/163 |
| 4,643,194 A * | 2/1987 | Fogarty | 600/481 |
| 5,042,161 A * | 8/1991 | Hodge | 33/501.45 |
| 5,044,951 A * | 9/1991 | Sheridan | 433/72 |
| 5,471,756 A * | 12/1995 | Bolanos et al. | 33/501.45 |
| 5,657,764 A * | 8/1997 | Coulter et al. | 600/591 |
| 5,697,886 A * | 12/1997 | Von Iderstein | 600/29 |
| 5,752,522 A * | 5/1998 | Murphy | 600/587 |
| 5,800,390 A * | 9/1998 | Hayakawa et al. | 604/93.01 |
| 6,027,442 A * | 2/2000 | Von Iderstein | 600/29 |
| 6,322,526 B1 * | 11/2001 | Rosenman et al. | 600/587 |

(Continued)

FOREIGN PATENT DOCUMENTS

| EP | 0584489 A1 * | 3/1994 | A61B 1/00 |
|---|---|---|---|
| GB | 2318513 A * | 4/1998 | A61B 5/22 |

OTHER PUBLICATIONS

Balke et al. "Anatomy of the reproductive tract of the female African elephant with reference to development of techniques for artificial breeding" J. Reprod. Fert. (1988) 84, 485-492.*

(Continued)

*Primary Examiner* — Sean Dougherty
*Assistant Examiner* — Michael C Stout
(74) *Attorney, Agent, or Firm* — Montgomery, McCracken, Walker & Rhoads, LLP; James L. Gannon, II

(57) ABSTRACT

A urethra gauge for measuring an inner size of a urinary tract. The gauge permits a clinician to measure the size of the urethral lumen (proximal to an outer orifice of the urethra) before a catheterization is performed. Selecting a properly-sized catheter for insertion into a patient by measuring the size of the urethral lumen before performing a catheterization is believed to reduce: (1) catheter-associated-urinary-tract infections; (2) urethral injuries due to inserting a catheter that is too large for the urethra; and/or (3) leakage associated with catheters that are too small for a particular patient.

10 Claims, 4 Drawing Sheets

(56) References Cited

U.S. PATENT DOCUMENTS

| | | | |
|---|---|---|---|
| 6,450,976 B2* | 9/2002 | Korotko et al. | 600/587 |
| 6,458,155 B1* | 10/2002 | Van Nguyen et al. | 623/2.11 |
| 7,998,093 B2* | 8/2011 | MacDonald | 600/587 |
| 2002/0010440 A1* | 1/2002 | Segesser | 604/272 |
| 2002/0032391 A1* | 3/2002 | McFann et al. | 600/585 |
| 2004/0102722 A1* | 5/2004 | Naghavi | 600/587 |
| 2004/0122462 A1* | 6/2004 | Bakos et al. | 606/191 |
| 2004/0216317 A1* | 11/2004 | Dalrymple | 33/566 |
| 2006/0020348 A1* | 1/2006 | Slemker et al. | 623/33 |
| 2006/0064039 A1* | 3/2006 | Griego et al. | 600/587 |
| 2007/0027408 A1* | 2/2007 | Fitzgerald et al. | 600/587 |
| 2007/0106181 A1* | 5/2007 | Mangiardi et al. | 600/587 |
| 2008/0161730 A1* | 7/2008 | McMahon et al. | 600/593 |
| 2008/0229597 A1* | 9/2008 | Malandain | 33/512 |
| 2009/0112263 A1* | 4/2009 | Pool et al. | 606/246 |
| 2009/0137870 A1* | 5/2009 | Bakos et al. | 600/116 |
| 2010/0234840 A1* | 9/2010 | Jackson et al. | 606/34 |
| 2011/0082392 A1* | 4/2011 | Mangiardi et al. | 600/587 |
| 2011/0251594 A1* | 10/2011 | Godin | 604/528 |

OTHER PUBLICATIONS

Stover, Charles. "Chapter XVIII. The Gauge of the Normal Urethra in Relation to the Permanent Cure of Urethral Stricture," Transactions of the Medical Society of the State of New York (1807- ), 1895, p. 162-166, The Medical Society of the State of New York, New York.

* cited by examiner

URETHRA GAUGE AND METHODS OF MANUFACTURE, AND OPERATION THEREOF

CROSS REFERENCE TO RELATED APPLICATIONS

The present patent application claims benefit of U.S. Provisional Application Ser. No. 61/061,086 filed on 12 Jun. 2008, incorporated herein by reference.

TECHNICAL FIELD

This invention relates generally to urinary catheters, and more specifically, to a device for measuring an inner circumference of the urethra, prior to inserting a urinary catheter, or other devices into the urinary tract.

BACKGROUND

A urinary catheter is a hollow tube inserted through the urethra into the bladder to empty it of urine. A catheter is commonly inserted into a patient to monitor the patient's urine and/or urine output. It is also inserted into a patient unable to urinate normally due to a medical condition, surgery, or sickness. The most distal part of the urinary tract is the urethra meatus, the most frequent place of insertion of a urinary catheter in a patient, whether male or female. The process of inserting the catheter into a patient is referred to as a catheterization, which is usually performed by a medical clinician, such as a nurse or physician.

Unfortunately, many patients develop a urinary-tract infection (UTI) after a catheterization; referred to as catheter-associated-urinary-tract infections. These "nosocomial" infections are estimated to account for approximately 40%—the majority—of all hospital-acquired infections in the United States. Catheter-associated UTI's drive up health care costs for the patient and hospital because more intensive medical care is needed, including additional medications to treat the infection and in some cases a longer hospital stay to allow the patient to recover. As of October 2008, however, Medicare and Medicaid no longer reimburse healthcare institutions for costs associated with treating hospital-acquired infections. To eliminate or reduce the incidence of catheter-associated UTI's, the medical community is focusing its attention on improving hand hygiene, and sterilization procedures associated with the use of catheters.

Despite the focus on better hygiene and sterilization procedures, catheter-associated-urinary-tract infections are not diminishing, and remain the leading type of disease process acquired while in a hospital, and the most costly nosocomial infection to treat. Such infections are becoming even more alarming as antibiotic-resistant infections increase in hospitals. Further, catheter-associated-urinary-tract infections often go undiagnosed and untreated, which can lead to myriad of life-threatening complications.

Therefore, what is needed is a way to reduce the quantity and incidence of catheter-associated-urinary-tract infections.

SUMMARY

The hollow-tube portion of a urinary catheter is offered to health-care providers in different circumferences. The relative size of urinary catheters is typically described using French Units (Fr), which is roughly equal to the circumference of a catheter in millimeters. For example, a urinary catheter generally comes in two primary sizes for adult humans in the Unites States with no known or special urinary conditions: large (18Fr) or small (16Fr).

Heretofore, before a clinician performs a catheterization, the clinician selects one of these two primary-catheter sizes—large (18Fr) or small (16Fr)—without knowing which size is best suited for the patient.

In other words, the clinician generally uses a two-size-fits-all approach for almost all adult catheterizations performed in the U.S., and selects one of the two aforementioned sizes based on a guess of which size is appropriate.

It is extremely difficult, however, to guess the size of a patient's inner urethra simply by viewing a patient's external features. For instance, a large individual may have a urethra with a small-inner circumference, whereas a petite individual may have a urethra with a larger-inner circumference. Further, even an individual's internal circumference may have a size and complexity that varies over time. For example, frequent catheterizations can lead to an enlarged urethral-lumen circumference for some patients, regardless of the patient's otherwise external features or appearance.

So, thus the inventor has recognized a problem that clinicians are overlooking when performing catheterizations: clinicians are often inserting the wrong sized catheter into the urethra, because clinicians are not measuring the size of the urethra lumen before inserting a catheter therein.

That is, the clinician is inserting a catheter that is either too large or too small for a patient's urethra, based purely on an accepted standard-of-care practice. The inventor believes that insertion of the wrong-sized catheter into a patient is a leading-contributing factor to catheter-associated-urinary-tract infections and other ailments such as pain and discomfort to the patient.

For instance, a catheter that is too large relative to a patient's urethra may cause a urethral injury; such as, stretching, tearing, or abrading of the urethra. Any of these urethral injuries can result in pain, and allows a hostile organism to invade the body at the site(s) of injury. Even slight microscopic tears are enough for a hostile organism to invade the body through an injury-induced "portal of entry".

On the other hand, when a catheter is too small relative to the size of a patient's urethra, spaces are created between the exterior surface of the catheter's tubing, and the inside of the urinary tract. So, urine or other matter (e.g., blood, salt, sand, secretions, microorganisms, bacteria, etc.), can leak into any of these unoccupied spaces, creating a "hostile environment" in which particles of matter are drawn, and aggregate through a cascade effect.

Other environmental factors of the urethra, such as pH, temperature, moisture, can further exacerbate conditions associated with infection when a catheter is not properly sized to fit precisely within a patient's urethra.

To address the above-discussed deficiencies, described herein is a urethra gauge for measuring the inner circumference of the urinary tract. The gauge permits a clinician to measure the size of the urethral lumen (proximal to an outer orifice of the urethra) before a catheterization is performed. Selecting a properly-sized catheter for insertion into a patient by measuring the size of the urethral lumen before performing a catheterization is believed to reduce: (1) catheter-associated-urinary-tract infections; (2) urethral injuries due to inserting a catheter that is too large for the urethra; and/or (3) leakage associated with catheters that are too small for a particular patient.

In one embodiment, the gauge includes a rod that has a conical shape, with a progressively increasing cross-sectional circumference from a smaller distal end to a larger-proximal end. In other words, an outer surface of the rod progressively widens in cross-sectional girth from the smaller-distal end of the rod to the larger-proximal end.

Accordingly, a clinician is able to insert the smaller-distal end of the rod into the urethra first. Because the larger-proximal end is larger and of a greater cross-sectional circumference than the opening of a urethra, penetration will stop at the point where resistance is met, and/or when the inner circumference of the urethra is coextensive with the outer surface of the rod. Based on this point of resistance and/or when the inner circumference of the urethra is coextensive with the outer surface of the rod, it is possible to determine the inner circumference of the urethra.

In one embodiment, the rod may include indicia marked thereon with sequentially graduated sizes corresponding to the increasing cross-sectional circumference of the rod. Based on markings on the rod, it is possible to obtain a visual indication of a size on the rod corresponding to a point on the rod that approximately aligns with a demarcation line between the exterior and interior of the urethra—when resistance is observed and/or when the inner circumference of the urethra is coextensive with the outer surface of the rod.

In another embodiment, the rod may be used in conjunction with an agent (such as Povidone-iodine, also known as PVP-I) or other suitable agent, such an antibacterial solution. The agent is applied to the area of the urethra orifice prior to inserting the rod. In yet another embodiment, this agent acts as a dye or marker, leaving a visual indication of how far the rod was actually inserted into the urethra, after the rod is removed from the patient—typically when resistance is observed and/or when the inner circumference of the urethra is coextensive with the outer surface of the rod.

Also, in certain embodiments, after the rod is removed from the urethra, it can be aligned with a measuring device. The measuring device includes indicia thereon with sequentially graduated sizes indicating a relative internal circumference of a urethra. So when the rod is aligned with the measuring device, with a distal-end of the rod aligned with a start of a measurement scale, clinicians can obtain an accurate measurement of the circumference of the urethra, by ascertaining a demarcation point where the dye and unmarked portion of the rod meet. This demarcation point provides an indication of a circumference of the inner urethra.

This invention, thus, eliminates guessing when performing a catheterization. By providing an exact measurement of the urethra, it is possible to insert a catheter that is properly sized for the patient, before performing a catheterization. This eliminates the potential for inserting a catheter that is (i) too large in relation to a patient's urethra, and may cause a urethral injury or (ii) too small in relation to a patient's urethra, and may cause leakage of urine into the space surrounding the catheter and the urethra. The urethra gauge described herein should ultimately reduce catheter-associated-urinary-tract infections.

Additional exemplary implementations and features/advantages are described in the Detailed Description in conjunction with the accompanying drawings below. The scope of the invention is recited in the Claims.

BRIEF DESCRIPTION OF THE DRAWINGS

The detailed description is explained with reference to the accompanying figures. In the figures, the left-most digit(s) of a reference number identifies the figure in which the reference number first appears. It should be noted that the figures are not necessarily drawn to scale and are for illustration purposes only.

DETAILED DESCRIPTION

Introduction

Reference herein to "one embodiment", "an embodiment", "an implementation" or "one implementation" or similar formulations herein, means that a particular feature, structure, operation, or characteristic described in connection with the embodiment, is included in at least one embodiment of the present invention. Thus, the appearances of such phrases or formulations herein are not necessarily all referring to the same embodiment. Furthermore, various particular features, structures, operations, or characteristics may be combined in any suitable manner in one or more embodiments.

In the following description, for purposes of explanation, specific numbers, materials and configurations are set forth in order to provide a thorough understanding of the present invention. However, it will be apparent to one skilled in the art that the present invention may be practiced without each specific example. In other instances, well-known features are omitted or simplified to clarify the description of the exemplary embodiments of the present invention, and thereby, to better explain the present invention.

The inventor intends these embodiments and implementations to serve as representative illustrations and examples. The inventor does not intend these embodiments to limit the scope of the claims; rather, the inventor has contemplated that the claimed invention might also be embodied and implemented in other ways, in conjunction with other present or future technologies.

As used herein the term "circumference" means a distance measured around an object or an orifice. As the exact shape of a urethra varies, the term "circumference" is not meant to exclude non-circular shapes. Furthermore, circumference may be measured in any fashion.

Exemplary Gauge

Figure 1:
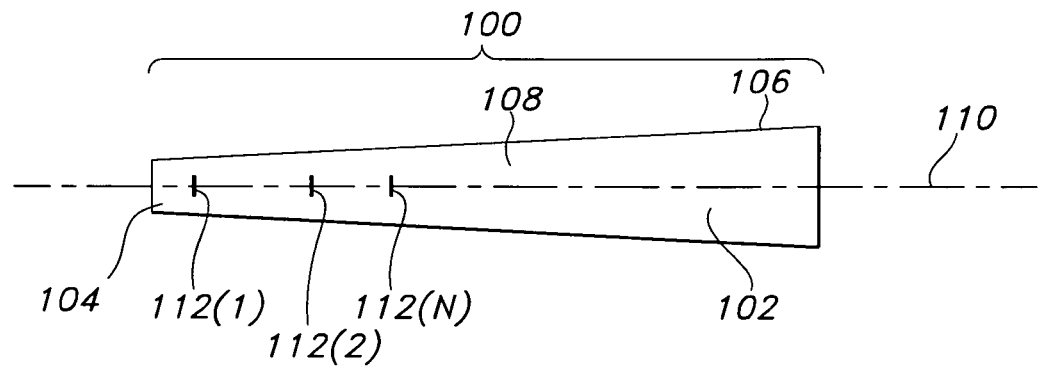
FIG. 1 is a side view of a urethra gauge for determining an internal circumference of a urethra.

FIG. 1 is a side view of a gauge 100 for determining the size of the internal portion of a urethra. Although in many of the examples herein gauge 100 is described with reference for use with an adult-human patient, it will become apparent to those skilled in the art, after having the benefit of this disclosure, that a gauge of the present invention may be configured for use with pediatric patients, or in a veterinarian setting with different types of animals. Thus, the term "urethra" is used generically.

Gauge 100 includes a rod 102 contoured for insertion into a urethra for determining the size, such as the circumference, cross-sectional area, diameter, perimeter, or boundary of the urethral lumen. In one embodiment, rod 102 is formed of a flexible or stiff material, or a combination of materials, such as rubber, polymer(s), polyurethane, wood, cellulose and cellulose-derivative, glass, metal, cardboard, plastic, composites thereof, or other suitable materials or combinations of materials, as would be appreciated by those skilled in the art having the benefit of this disclosure. Rod 102 may also be hollow, solid, or semisolid.

Rod 102 includes a distal-end point 104 and a proximal-end point 106. In one embodiment, rod 102 has an outer-peripheral surface 108 that is generally conical in shape. That is, rod 102 has an outer-peripheral surface 108 with a progressively increasing cross-sectional girth (i.e., cross-sectional area) or circumference extending from the distal-end point 104 to the proximal-end point 106 that widens outwardly. The girth is measured with respect to a longitudinal axis 110 of the rod 102.

In one embodiment, rod 102 is generally conical in shape with a narrow distal end and a wider proximal end. Rod 102 may also be curved, straight, or may incorporate other shapes or forms other than cylindrical, such as tubular, triangular, rectangular, pentagonal, octagonal, and other various three-dimensional shapes as would be readily appreciated by those skilled in the art, after having the benefit of this disclosure. The texture of the outer surface 108 of the gauge 100 or a portion of the outer surface 108 of gauge 100 may be smooth or rough, or of varying textures, such as for ease of handling the gauge 100 and/or inserting the gauge 100 into the urethra.

In an alternative embodiment, not shown, it is possible for the rod 102 to have varying narrowing and/or widening of rod 102 girth, at various intervals relative to the rod's longitudinal axis 110. In another embodiment, rod 102 may also be contoured or curved to fit inside the urethra of male or female anatomies.

In general, the girth or circumference of outer-surface 108 of rod 102 at the distal-end point 104 corresponds to a first-potential size for the inner circumference of a urethra. In one embodiment, the first-potential size is the smallest potential size that can be measure by gauge 100. As depicted in FIG. 1, the location of distal-point 104 is at the end of rod 102, but it could also be located at other points closer to the proximal-end point. Thus, the term "proximal-end point" is intended to convey a location on rod 102 that is not necessary at a furthest end of rod 102.

On the other hand, the circumference of outer-surface 108 of the rod 102 at the proximal-end point 106 corresponds to a second-potential size for the internal circumference of a urethra larger than the first-potential size. In one embodiment, this second-potential size is the largest potential size that can be measured by gauge 100. As depicted in FIG. 1, the location of proximal-end point 106 is at an end of rod 102, but it could also be located at other points closer to distal-end point 106. Thus, the term "distal-end point" is intended to convey a location on rod 102 that is not necessary at a furthest end of rod 102.

Between distal-end point 104 and the proximal-end point 106, are an array of graduations 112(1), 112(2) . . . 112(N), such as points, lines, markings located along the outer surface 108 of rod 102 which correspond to a plurality of potential sizes (circumferences) for the internal circumference of a urethra. These sizes correspond to any urethra size larger than the first-potential size, but less than the second-potential size.

Figure 2:
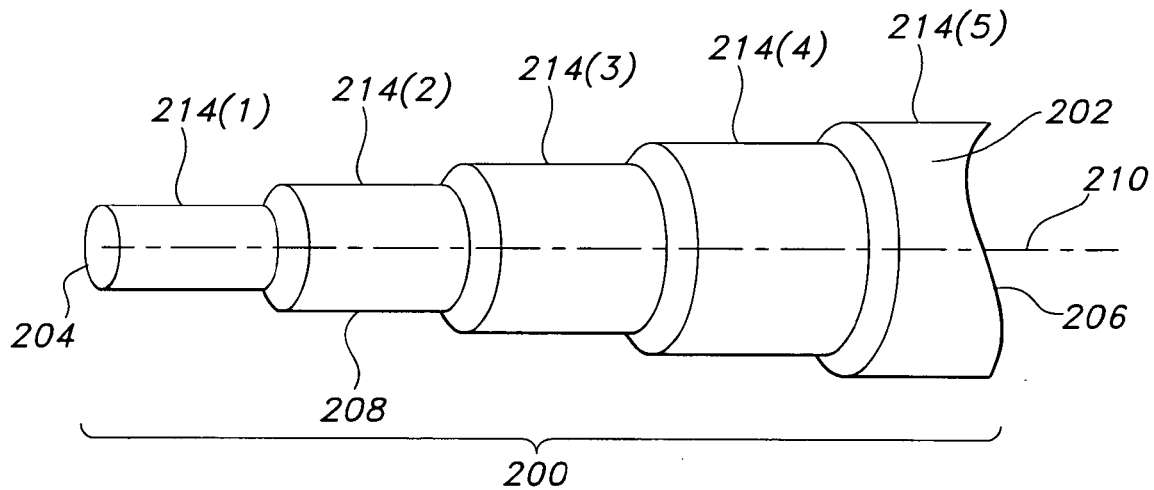
FIG. 2 shows an enlarged distal-end portion of a rod for a urethral gauge with terraced steps along its outer-peripheral surface.

Although FIG. 1 shows rod 102 as having a smooth and steady outer-surface 108, it is possible for the outer-surface 108 to have graduated widths. For instance, FIG. 2 depicts another embodiment of, shown as gauge 200. In one embodiment, rod 202 of gauge 200 may also have terraced steps 214(1), 214(2), 214(3), 214(4), 214(5), etc., which correspond to a plurality of potential sizes for the internal circumference of a urethra. In particular, FIG. 2 shows a distal-end portion 204 of rod 202 with terraced steps 214 along its outer-peripheral surface 208. Each of the terraced steps 214 correspond to a graduated size corresponding to an inner circumference of the urethra.

A can be seen by embodiments shown in FIGS. 1 and 2, and based on the foregoing, the shape of the urethra-gauge rod may vary.

In one embodiment, the rod is approximately 2.5 inches long. But as would be appreciated by those skilled in the art, the rod may be larger or smaller than 2.5 inches and may also differ in ranges of girths or circumferences. For example, the rod girth may include circumferences ranging from 3 Fr to 10 Fr, useful for pediatric use, whereas for adults, circumferences generally will range from 10 Fr to 34 Fr. Other ranges, larger or smaller, may be included.

Figure 3:
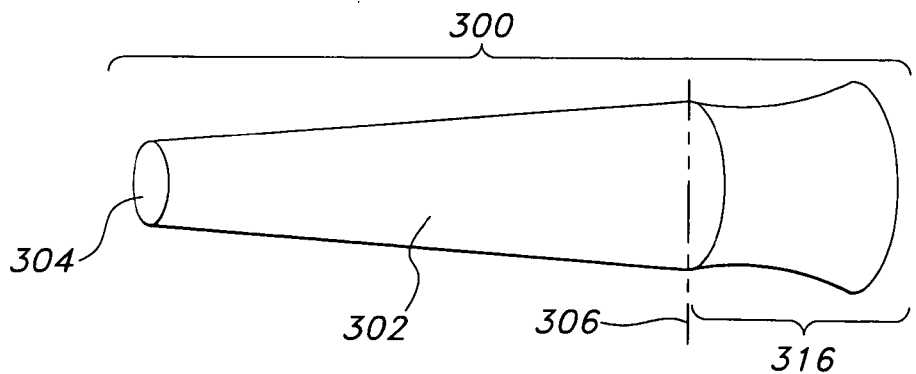
FIG. 3 shows a urethra-gauge embodiment with a handle.

Turning to FIG. 3, another embodiment is shown as gauge 300, which may include an optional handle 316 portion positioned proximal with the proximal-end point 306. Handle 316 allows a clinician to readily grasp gauge 300 when wearing surgical gloves. In one embodiment, handle 316 may be configured integral to rod 302, forming an extension thereof, or fastened (directly or indirectly) to rod 302. In another embodiment, additional attachments/configurations can be assembled with gauge 300, as would be desired by those skilled in the art.

Figure 4:
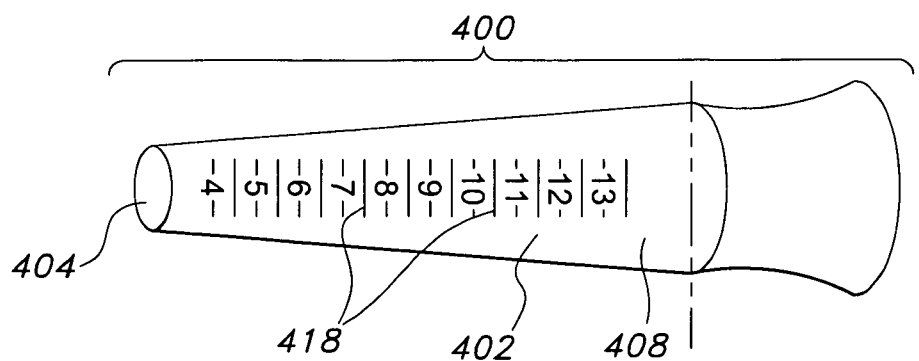
FIG. 4 shows another embodiment of the urethra gauge with measurement indicia imprinted on an outer-surface.

FIG. 4 shows yet another embodiment of the urethra gauge, shown as gauge 400, wherein measurement indicia 418 imprinted, or formed thereon, on the outer-surface 408 of rod 402. In one embodiment, measurement indicia 418 may represent any girth or circumference, and be in any scale, such as the French Catheter Scale (Fr), millimeters, centimeters, inches, or other SI or metric units generally used by those skilled in the art. In another embodiment, measurement indicia 418 may be displayed by any suitable means allowing one skilled in the art to determine the size of the urethra opening, such as by visual markings on rod 402, or via a display on an LCD screen, or by an audible tone or signal capable of indicating a desired value or measurement.

Figure 5A:
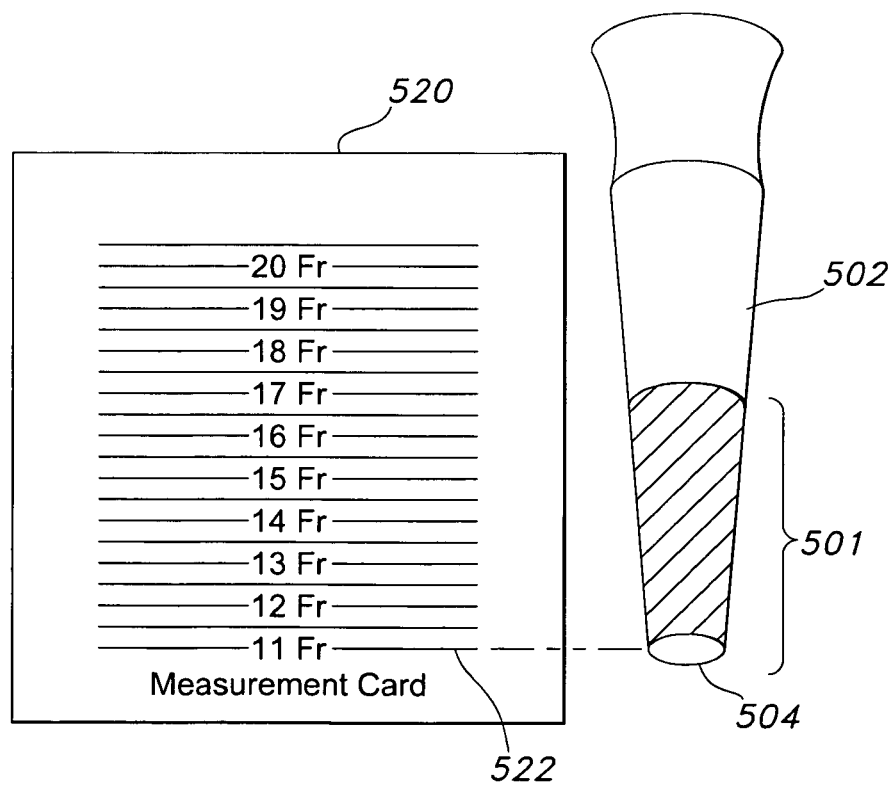
FIG. 5A shows a measurement device that may be used in conjunction with the urethra gauge.
Figure 5B:
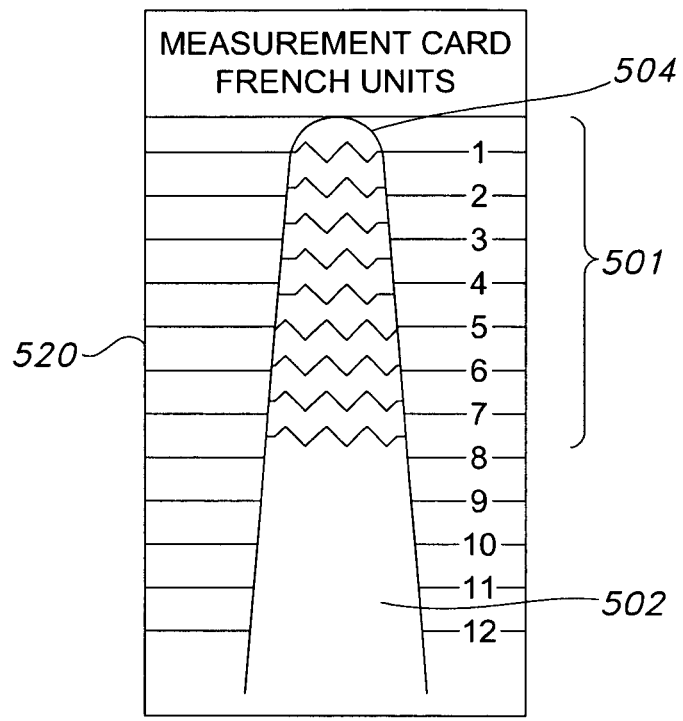
FIG. 5B shows another embodiment of a measurement device for use in conjunction with the urethral gauge.

FIGS. 5A and 5B show an embodiment of gauge 500 accompanied by a measurement device 520 that may be used with rod 502, if neither gauge 500 nor rod 502 are configured to include measurement indicia. In one embodiment, the measurement device 520 is a card; but as would be appreciated by those skilled in the art, measure device 520 may include other suitable devices, such as a ruler-type device, a tubular housing containing suitable measuring graduations that can be aligned complimentary to the contours of rod 502, or various other types of measurement devices.

As shown in FIG. 5A, measurement indicia are spaced apart at different intervals of a graduated scale along measurement device 520, ranging from a smallest circumference to largest circumference of a urethra. In one embodiment, when rod 502 is inserted into the urethra following use of a stain on the urethral surface are and is removed from the urethra, the gauge will contain traces of the stain used on the urethral surface. The stained portion 501 of rod 502 (shown in more detail in FIG. 5B) can be aligned with measuring device 520 to determine urethra size. For example, when stained portion 501 of rod 502 is aligned with measuring device 520, with the distal-end point 504 of rod 502 aligned with a start 522 of a measurement scale, clinicians can obtain an accurate measurement of the circumference of the urethra, if they know how far the rod 502 penetrated the inner urethra before resistance is observed and/or when the inner circumference of the urethra (proximal to a start of the urethra lumen with respect to the orifice of the urethra) is coextensive with the outer surface of the rod 502.

Figure 6A:
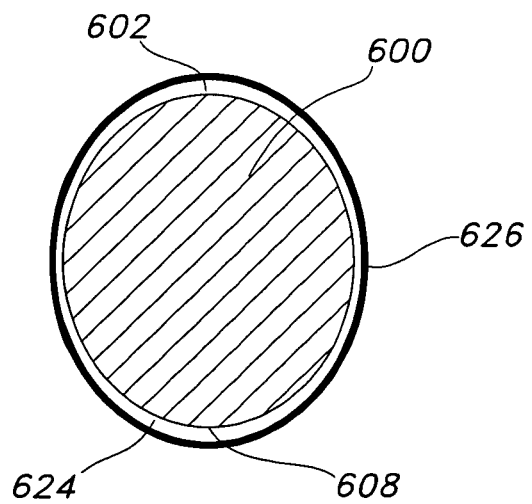
FIGS. 6A and 6B show a cross-sectional view of a rod of the invention when inserted inside a urethra, typically when resistance is observed when penetrating the urethra and a side-view of the rod penetrating the urethra.
Figure 6B:
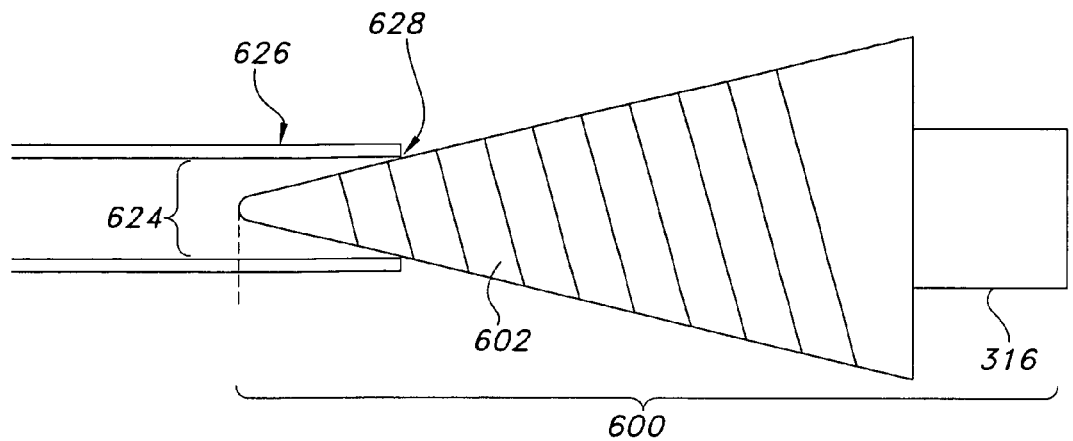

Turning to FIGS. 6A and 6B, an inner circumference 624 of another embodiment of gauge 600 is shown via cross-sectional view (6A) and side-view (6B). As depicted in FIG. 6A, a point or coextensivity 628—or point of resistance—is observed as rod 602 is placed in a urethra 626, the inner circumference 624 of urethra 626 is coextensive with the outer surface 608 of rod 602. FIG. 6B shows a side-view of another embodiment of gauge 600, highlighting the point of coextensivity 628 formed as gauge 202 is coextensive with the internal circumference 624 of urethra 626.

Figure 7:
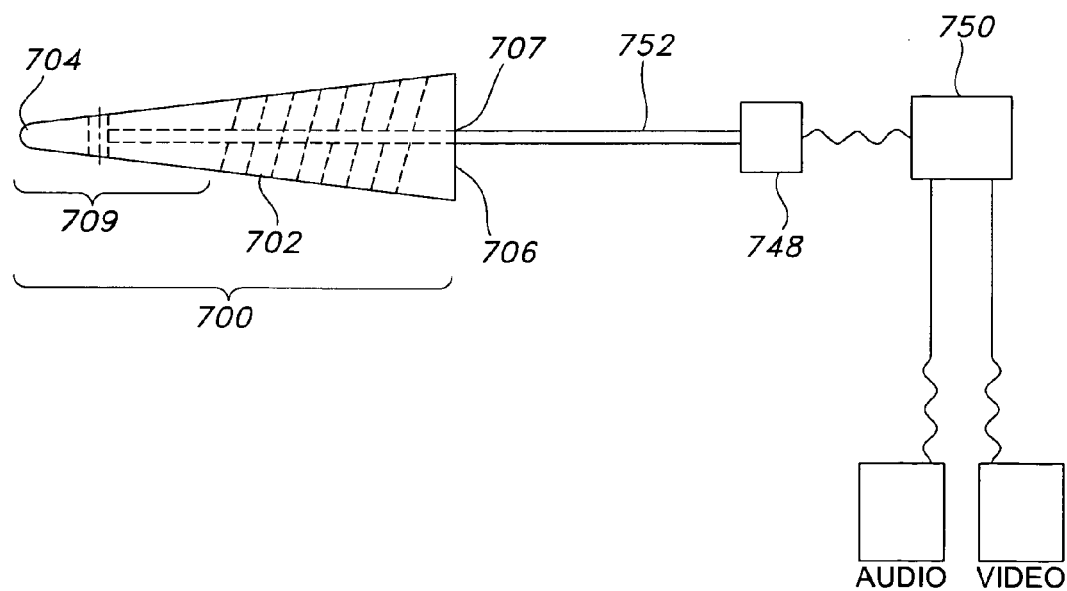
FIG. 7 shows another embodiment of the urethra gauge and a system for automated measurement of urethral circumference.

In another embodiment shown in FIG. 7, the measurement of the urethra is made by measuring a change in pressure in the urethral lumen as the gauge 700 is inserted into the urethra. Pressure measurement may be accomplished by equipping gauge 700 with a sensing device capable of providing a visual and/or audible indication that due to the pressure measured, gauge 700 is in an optimal—or alternatively, non-optimal—place for measuring the circumference of the urethral lumen.

In one embodiment, urethra gauge 700 for determining an internal circumference of a urethra, comprises a rod 702 having a distal-end point 704 and a proximal-end point 706, with a bored-out or hollowed-out portion 707 of the proximal end 706 of the rod 702 configured to detect pressure applied to at least a portion of rod 702 upon insertion of rod 702 into the urethra, such as detection of pressure exerted at an amount corresponding to positioning of a portion 709 of rod 702 within the inner urethra, such that an inner circumference of the urethra is coextensive with an outer surface of rod 702, which is signaled by a visual display or an audible tone, or a combination thereof.

In one embodiment, gauge 700 is configured to sense a pressure change in the urethral lumen. Gauge 700 includes a rod 702 with a distal end 704 closed to the exterior and a proximal end 706 that is hollow on the interior, such as through a bore, to create an environment of comparatively low-atmospheric pressure. A pressure transducer 748 is, directly or indirectly, coupled to rod 702 at a proximal end 706 of rod 702. A hollowed-bored gauge 700 coupled to a pressure-sensing device 750 is capable of sensing a change in pressure, such as exerted between the interior lumen of the urethra and the outer surface of rod 702, and transmits a signal, either by visual display or audible signal, that pressure has reached or exceeded a desired and/or predetermined threshold, such as when the circumference of the urethra is coextensive with an outer surface of the rod.

In one embodiment, a hose 752 is connected between pressure-sensing device 750 and proximal end 706. A comparatively low-atmospheric pressure is created in the hollow-end portion (e.g., proximal end 706) of rod 702. When rod 702 is inserted inside the interior of the urethra, pressure increases to a point of that exceeds a predetermined threshold, which is indicative of reaching an optimal point for measuring the inner size of the urethra. As appreciated by those skilled in the art, any suitable pressure-measuring instrument (such as a manometer) may be connected, directly or indirectly to hose 752, to measure pressures exerted on rod 702. Pressure-sensing device 750 may include a processor configured to generate an audio and/or visual signal.

In another embodiment, not shown in figures, other measurement means can be coupled to audio-visual outputs for automated measurement of urethral circumference, such as by using a force meter.

In yet another embodiment, a chemiluminescent stain can be applied to the outer urethra surface prior to insertion of the urethral gauge. The chemiluminescent stain can be used to mark the point of coextensivity of the outer surface of the gauge with the urethral lumen upon and can then be subjected to analysis with a spectrometer, which can separate differences in color of gauge and the stain and determine the precise line of demarcation on the gauge that corresponds to a measurement such as French Unit. In one embodiment, output of the resulting measurement can be presented in visual format, such as on a computer monitor, or tabulated such as in the form of a printout from the spectrometer or an attached printing device. In another embodiment, the spectrometer can be connected to one of various networks in a hospital computing system or electronic medical record system so that information can be conveniently stored electronically in a patient's file.

Having introduced a urethra gauge as described herein, it is possible to describe how it may be used by a clinician or other medical personnel.

EXEMPLARY METHODS OF USE

Described in this section is a method for measuring the internal circumference of the urinary tract to determine a correct-sized catheter, or other device, to insert in a patient's urethra. It is appreciated that certain operational steps may be omitted, additional operational steps not described added, or the exact order of steps may be performed differently.

a.) While maintaining sterile techniques:
  i. Don personal protective equipment (magnifying glasses/loops), and sterile gloves.
  ii. Position patient appropriately, normally in the supine/lithotomy position.
  iii. Remove patient garments to visualize the region of the pubic genitalia.
  iv. Assistant on right side of patient holding knee bent with the patient foot planted on stretcher and knee abducted from midline, holding right arm of patient if necessary.
  v. Assistant on left side of patient holding knee bent with the patient foot planted on stretcher and knee abducted from midline, holding left arm of patient if necessary.
  vi. Licensed healthcare worker places magnifying glasses/magnifying loops over eyes.
  vii. Licensed healthcare worker opens sterile container containing gauge, and places package on a portable table.
  viii. Remove sterile drape from package.
  ix. Drape sterile drape around and about the genitalia, the genitalia should be clearly visualized thru the opening in the drape, with patient in the supine position, with the assistance of two unlicensed assistants each holding a leg and potentially an arm if necessary.
  x. Open antibacterial agent and cover the 3 cotton balls with the antibacterial agent. (Use Povidone-iodine (PVP-I) unless the patient is allergic to Iodine then use another readily available antibacterial agent or staining agent.)
  xi. Pick up the lubricant and open and squeeze into the container in lubricant area.
  xii. Pick up plastic forceps and remove 1 cotton ball that is covered in the antibacterial agent of choice.
  xiii. Do not use iodine if the patient has an iodine allergy, Clean the urethra opening with PVP-I or another readily available antibacterial agent. Use a circular motion and thoroughly cleanse the area.
  xiv. Dispose of cotton ball.

xv. Retrieve another, clean cotton ball from the package using plastic forceps.

xvi. Repeat step XII, not using iodine if patient has an iodine allergy. Clean the urethra opening with PVP-I or another readily available antibacterial agent. This time wipe in a counterclockwise motion.

xvii. Dispose of the second cotton ball.

xviii. Retrieve a third cotton ball from package using plastic forceps.

xix. Repeat step XII, do not use iodine if patient has an allergy. Clean the urethra opening with PVP-I or another readily available antibacterial agent. This time wipe from top to bottom of urethral opening.

xx. Dispose of third cotton ball.

xxi. Grasp urethra gauge and cover it with a lubricant.

xxii. Insert gauge into urethra smallest end (distal end) first until resistance is met.

xxiii. IF PVP-I is used it will act as a stain, and leave a mark on the gauge outer surface corresponding to the internal perimeter or internal circumference of the urethra.

xxiv. Remove the gauge and place on the laminated index-card-ruler (or other measuring device). Determine the corresponding position on the measurement device by aligning the PVP-I dyed-marking on the gauge to the measuring device, which will illustrate the measurement of the perimeter/circumference of the internal-urethral opening. The length of the measurement obtained corresponds to the perimeter of the urethra at point of measurement.

xxv. With this measurement in hand, select and insert an appropriate catheter or other device in patient.

By following the preceding prescriptions the appropriate size catheter will be used with less injury and risk of infection resulting to the patient.

In one exemplary embodiment, the gauge is manufactured and prepared according to standard methods in the industry, such as by injection into a mold (mold-injection) under pressure by way of compression. In one embodiment the mold is prepared using a laser that cuts the specific shape of the mold desired, such as a mold corresponding to a conical-shaped rod, as shown in FIGS. 1-5 from a block of steel.

In one embodiment, the resulting gauge is subjected to sterilization, prior to—or concomitant with—packaging of the gauge. Suitable sterilization methods include those methods known in the art, such as sterilization by heat, steam, cold vapor, gas, foam or via exposure to ultraviolet light or radiation. Suitable packaging materials for the urethra gauge include packaging materials as known in the art for maintaining sterility of contents secured therein; Suitable packaging materials for encasing the gauge include paper, foil, or plastic, blister packs, tyvek, glass or other suitable natural or synthetic materials that may be known in the art.

It is to be understood that the present invention is not limited to the embodiments described above, but encompasses any and all embodiments within the scope of the subjoined Claims and their equivalents.

What is claimed is:

1. A system for determining a measured internal size of a urinary tract lumen proximate to a urethral oval outer opening of a patient, prior to urinary catheterization of said patient, the system comprising:
   a gauge for insertion into the urethra, constructed of a single rod-shaped measuring device having
      a distal-end, configured for insertion into a urethra and which forms the point of initial insertion into the outer opening of the urethra;
      a proximal-end of progressively increasing cross-sectional circumference relative to the distal end, until an inner circumference of the urethra is coextensive with an inserted portion of the gauge; and
      a solid or semisolid oval cross-section, wherein length of a cross-section of the gauge is greater than width at a widest point thereof; and
      wherein an array of indicia are located on an outer-peripheral surface of the gauge, such that each indicia corresponds to a potential measured internal circumference, area, diameter, perimeter or boundary of the urethral lumen; and
      wherein the gauge is contoured for insertion into the urethra only until resistance is first encountered without injury to the patient; and
   a stain for application to an outer surface of the urethra and a portion of the gauge coextensive with the stained outer surface of the urethra when the gauge has been inserted into the urethra only until resistance is first encountered without injury to the patient.

2. The in system of claim 1, wherein the the gauge has a conical longitudinal shape.

3. The system of claim 1, wherein the gauge is formed of a flexible material.

4. The system of claim 1, wherein the gauge is made from material selected from the group consisting of: rubber, polymer, silicone, glass, wood, plastic, metal, cardboard, polypropylene, polyurethane, and one or more combinations thereof.

5. The system of claim 1, wherein the gauge is sterile.

6. The system of claim 1, wherein the gauge is packaged in a sterile container.

7. A method of measuring the internal size of a urinary tract lumen proximate to a urethral oval outer opening of a patient using a gauge constructed of a single rod-shaped measuring device having
   a distal-end, configured for insertion into a urethra and which forms the point of initial insertion into the outer opening of the urethra;
   a proximal-end of progressively increasing cross-sectional circumference relative to the distal end, until an inner circumference of the urethra is coextensive with an inserted portion of the gauge; and
   a solid or semisolid oval cross-section, wherein length of a cross-section of the gauge is greater than width at a widest point thereof; and
   wherein an array of indicia are located on an outer-peripheral surface of the gauge, such that each indicia corresponds to a potential measured internal circumference, area, diameter, perimeter or boundary of the urethral lumen; and
wherein the gauge is contoured for insertion into the urethra only until resistance is first encountered without injury to the patient, the method comprising:
   grasping the gauge contoured for insertion into the urethra, inserting the distal-end of the gauge into the urethra of the patient until resistance is first met
   applying a stain to a surface of the urethra;
   staining a portion of the gauge coextensive with the stained urethra when the gauge is inserted therein until resistance is first met;
   removing the gauge from the urethra without injury to the patient; and
   determining the internal circumference area, diameter, perimeter, or boundary of the urethral lumen by viewing and recording indicia on the stained portion of the gauge corresponding to a measured circumference, area, diameter, perimeter or boundary of the urethral lumen at the point at which resistance to insertion was met.

8. The method of claim 7, wherein viewing the stained portion of the gauge further comprises:
aligning the distal-end of the gauge with a start of a measurement scale and
determining a position on the measurement scale which corresponds to a length of the stained portion of the gauge, thereby illustrating the measured internal circumferential size of the urethra.

9. The method of claim 1, wherein the stain is a chemiluminescent stain.

10. The method of claim 7, wherein the stain is a chemiluminescent stain.

* * * * *